(12) United States Patent
Littich et al.

(10) Patent No.: US 10,501,429 B2
(45) Date of Patent: Dec. 10, 2019

(54) GLYCITAN ESTERS OF UNSATURATED FATTY ACIDS AND THEIR PREPARATION

(71) Applicant: Elevance Renewable Sciences, Inc., Woodridge, IL (US)

(72) Inventors: Ryan A. Littich, Shorewood, IL (US); Timothy Montavon, Palatine, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 713 days.

(21) Appl. No.: 14/681,324

(22) Filed: Apr. 8, 2015

(65) Prior Publication Data

US 2015/0307469 A1    Oct. 29, 2015

Related U.S. Application Data

(63) Continuation of application No. 14/203,039, filed on Mar. 10, 2014, now Pat. No. 9,045,447.

(60) Provisional application No. 61/783,319, filed on Mar. 14, 2013.

(51) Int. Cl.
*C07D 307/20* (2006.01)
*C07C 51/347* (2006.01)

(52) U.S. Cl.
CPC .......... *C07D 307/20* (2013.01); *C07C 51/347* (2013.01)

(58) Field of Classification Search
CPC .................................................. C07D 307/20
USPC ....................................................... 549/478
See application file for complete search history.

(56) References Cited

U.S. PATENT DOCUMENTS

| | | | |
|---|---|---|---|
| 4,297,290 A | 10/1981 | Stockburger | |
| 4,545,941 A | 10/1985 | Rosenburg | |
| 3,258,440 A | 6/1999 | Burleigh et al. | |
| 2009/0264672 A1 | 10/2009 | Abraham et al. | |
| 2010/0145086 A1 | 6/2010 | Schrodi et al. | |
| 2011/0113679 A1 | 5/2011 | Cohen et al. | |

FOREIGN PATENT DOCUMENTS

| | | |
|---|---|---|
| CN | 101474403 | 7/2009 |
| EP | 0601836 | 6/1994 |
| EP | 0692737 | 10/1996 |
| EP | 1623695 | 2/2006 |
| EP | 2239292 | 10/2010 |
| JP | 2004217920 | * 8/2004 |
| WO | WO 2008/048522 | * 4/2008 |

OTHER PUBLICATIONS

Jirglova et al., Langmuir, (2010), vol. 26(20), pp. 16103-16109.*
Submitted by applicant in U.S. Appl. No. 14/203,039.*
International Search Report and Written Opinion of the International Searching Authority, PCT Application No. PCT/US2014/022601, dated Aug. 1, 2014.
Jirglova et al, Langmuir, vol. 26(20), pp. 16103-16109 (2010).
Djigoue et al., Appl. Catal. A: General, vol. 368, pp. 158-162 (2009).
Mol, Green Chem., Royal Soc. Chemists, vol. 4, pp. 5-13 (2002).

* cited by examiner

*Primary Examiner* — Taofiq A Solola
(74) *Attorney, Agent, or Firm* — Kilpatrick Townsend & Stockton LLP

(57) ABSTRACT

A method is disclosed for making an unsaturated glycitan ester by reacting intramolecular condensates of glycitols having four or more carbons with a metathesis-derived unsaturated fatty acid in the presence of an alkaline catalyst and under conditions sufficient to form the aforesaid unsaturated glycitan fatty ester. A composition is also disclosed comprising a compound of the following structure:

wherein $R^1$ is hydrogen, alkyl, aryl or $(CH_2)_{1-9}$—$COOR^5$; wherein $R^5$ is wherein $R^2$, $R^3$ and $R^4$ are hydrogen, or —(O)C—$(CH_2)_m$—CH═CH—$R^1$ or —$(CH_2CH_2O)_n$H or mixtures thereof; wherein m is 1 to 9; and wherein n is 1 to 100.

12 Claims, No Drawings

GLYCITAN ESTERS OF UNSATURATED FATTY ACIDS AND THEIR PREPARATION

CROSS-REFERENCE TO RELATED APPLICATIONS

This application claims the benefit of U.S. Provisional Application No. 61/783,319 filed Mar. 14, 2013, the entire contents of which are hereby incorporated by reference.

BACKGROUND

Surfactants based on glycitan esters of fatty acids, most notably sorbitan esters of fatty acids, are gaining increasing attention due to their advantages over other surfactants with regard to their notable dermatological properties and good compatibility with standard products, as well as their favorable environmental profile. In addition, their low toxicity, good biocompatibility, and fast biodegradation make this class of molecules very attractive, not only for personal care products but also for a large range of technical applications.

More particularly, glycitan esters of unsaturated fatty acids are nonionic, amphiphilic materials that provide emulsifying, and wetting properties that are comparable to those of other nonionic surfactants. They are conventionally produced by reacting intramolecular condensates of glycitols having four or more carbons with a fatty acid. The fatty acids used to make such fatty acid esters are prepared by hydrolysis of triglycerides, which typically originate from animal or vegetable fats. Consequently, the fatty portion of the acid will typically have 6-22 carbons with a mixture of saturated and internally unsaturated chains. Depending on the source, the fatty acids often have a preponderance of $C_{16}$ to $C_{22}$ components. For instance, hydrolysis of soybean oil provides saturated palmitic ($C_{16}$) and stearic ($C_{18}$) acids and unsaturated oleic ($C_{18}$ mono-unsaturated), linoleic ($C_{18}$ di-unsaturated), and α-linolenic ($C_{18}$ tri-unsaturated) acids. The unsaturation in these acids has either exclusively or predominantly a cis-configuration. Thus, traditional sources of fatty acids used to produce saturated and unsaturated glycitan fatty esters generally have predominantly or exclusively cis-isomers and lack relatively short-chain (for example, $C_{10}$ or $C_{12}$) unsaturated fatty portions.

Improvements in metathesis catalysts (see J. C. Mol, *Green Chem.* 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain lengths and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecene, 9-decenoic acid, and 9-undecenoic acid.

SUMMARY

In one aspect, a method comprises making an unsaturated glycitan ester by reacting intramolecular condensates of glycitols having four or more carbons with a metathesis-derived unsaturated fatty acid in the presence of an alkaline catalyst and under conditions sufficient to form the aforesaid unsaturated glycitan fatty ester.

In another aspect, a composition comprises the following structure:

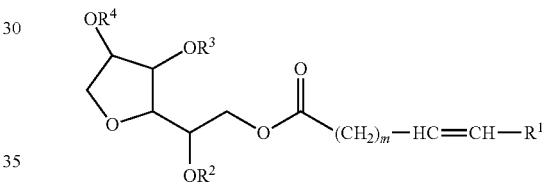

wherein $R^1$ is hydrogen, alkyl, aryl, or $(CH_2)_{1-9}$—$COOR^5$; and wherein $R^5$ is

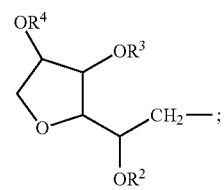

wherein $R^2$, $R^3$ and $R^4$ are hydrogen, or —(O)C—$(CH_2)_m$—CH=CH—$R^1$ or —$(CH_2CH_2O)_n$H or mixtures thereof; wherein m is 1 to 9; and wherein n is 1 to 100.

DETAILED DESCRIPTION

As used herein, the term "hydrocarbyl" or "hydrocarbyl group," when referring to groups attached to the remainder of a molecule of a metathesis-derived hydrocarbyl unsaturated acid refers to one or more groups having a purely hydrocarbon or predominantly hydrocarbon character. These groups may include: (1) purely hydrocarbon groups (i.e., aliphatic (alkyl), alicyclic, aromatic, branched, aliphatic- and alicyclic-substituted aromatic, aromatic-substituted aliphatic and alicyclic groups, as well as cyclic groups wherein the ring is completed through another portion of the molecule (that is, any two indicated substituents may together form an alicyclic group)); (2) substituted hydrocarbon groups (i.e., groups containing non-hydrocarbon substituent such as hydroxy, amino, nitro, cyano, alkoxy, acyl, halo, etc.); and (3) hetero groups (i.e., groups which contain atoms, such as N, O, or S, in a chain or ring otherwise composed of carbon atoms). In general, no more than about three substituents or hetero atoms, or no more than one, may be present for each 10 carbon atoms in the hydrocarbyl group. The hydrocarbyl group may contain one, two, three, or four carbon-carbon double bonds.

As used herein, the terms "natural oils," "natural feedstocks," or "natural oil feedstocks" may refer to oils derived from plants or animal sources. The term "natural oil" includes natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

As used herein, the term "natural oil derivatives" may refer to the compounds or mixture of compounds derived from the natural oil using any one or combination of methods known in the art. Such methods include but are not limited to saponification, fat splitting, transesterification, esterification, hydrogenation (partial or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, the terms "metathesize" and "metathesizing" may refer to the reacting of a feedstock in the presence of a metathesis catalyst to form a "metathesized product" comprising a new olefinic compound. Metathesizing may refer to cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, the terms "ester" and "esters" may refer to compounds having the general formula: R—COO—R', wherein R and R' denote any organic compound (such as alkyl, aryl, or silyl groups), including those bearing heteroatom containing substituent groups. In certain embodiments, R and R' denote alkyl or aryl groups. In certain embodiments, the term "ester" or "esters" may refer to a group of compounds with the general formula described above, wherein the compounds have different carbon lengths.

In certain embodiments, the product described herein is a composition comprising the following structure:

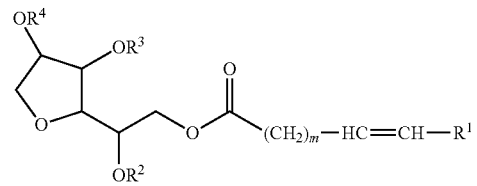

wherein $R^1$ is hydrogen, alkyl, aryl or $(CH_2)_{1-9}$—$COOR^5$; wherein $R^5$ is

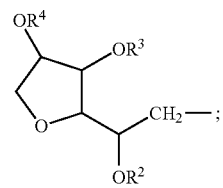

wherein $R^2$, $R^3$ and $R^4$ are hydrogen, or —(O)C—$(CH_2)_m$—CH=CH—$R^1$ or —$(CH_2CH_2O)_n$H or mixtures thereof; wherein m is 1 to 9; and wherein n is 1 to 100.

Preferably m is 7 or 9, and most preferably 7. Preferably, $R_1$, $R_2$, $R_3$, and $R_4$ are all hydrogen.

Alternatively, $R_1$ is $(CH_2)_{1-9}$—$COOR^5$ and $R^5$ is

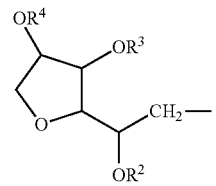

resulting in a di-glycitan diester.

Methods described herein contemplate the production of unsaturated fatty esters of glycitol intramolecular condensates, which intramolecular condensates have one to two mono-oxacyclic, 5- to 7-membered carbon-oxygen rings (cyclic ether rings), either 2, 3 or 4 hydroxyl groups, and being derivable from glycitols having four or more carbons. In general, the intramolecular condensates may be formed under the conditions of and during the fatty acid esterification reaction by using glycitol in the original reaction mixture or, preferably the intramolecular condensates may be used as such in the original reaction mixture. The intramolecular condensates, as stated above, may have one to two mono-oxacyclic, 5- to 7-membered carbon-oxygen rings, and at least two hydroxyl groups available to react with the unsaturated fatty acid or mixture of unsaturated fatty acids. The intramolecular condensates may be defined as compounds containing carbon-oxygen rings with one oxygen per ring (known as an oxido ring) and derivable from glycitol by intramolecular condensation. If only one molecule of water is removed by the intramolecular condensation, a monoanhydro derivative containing predominantly one carbon-oxygen ring is obtained. If the condensation removes two molecules of water from the polyhydric alcohol, a dianhydro compound containing predominantly two-carbon-oxygen rings is obtained. The number of nuclei in the ring and the number of oxido rings which are obtainable depend upon the configuration of the carbon atoms in the chain of the glycitol from which the intramolecular condensates are derived and upon the conditions of the reaction. It is possible to form dianhydro compounds containing carbon-oxygen rings having different numbers of nuclei, for example, a compound containing a 5- and a 6-membered ring.

The glycitols applicable for use in preparing the products described herein are of such structures that the intramolecular condensation described can take place in several different ways. Whether in any particular reaction mono- or dianhydro compounds predominate depends generally upon the conditions of the reaction, the time and temperature, and particularly the type of catalyst employed. As a result of the condensation of the glycitols, a mixture of the various intramolecular condensates may be formed. As examples of glycitols suitable for use, any four or more carbon atom, aliphatic, straight chain, polyhydric alcohol may be employed, but it is preferred to use a six-carbon straight-chain hexitol. It is also preferred to use a hexitol such as mannitol, sorbitol, and dulcitol due to their availability.

It is to be understood that the intramolecular condensation reaction by which the present intramolecular condensates are formed may take place between any of the non-adjacent hydroxyl-bearing carbon atoms of the glycitol. The furan ring is the predominantly obtained product from the intramolecular condensation reaction under usual conditions, although smaller amounts of other intramolecular condensation products of both the mono- and dianhydro type may be present. The intramolecular condensates of the various glycitols may be designated by names derived from the stem of the parent alcohol by substituting for the characteristic suffix "itol" for the alcohol, the suffix "itan" for the cyclic mono-anhydro derivative and "ide" for the dianhydro intramolecular condensation derivatives, thus: mannitol, mannitan, mannide; sorbitol, sorbitan, sorbide; dulcitol, dulcitan, dulcide, etc. It is to be understood that wherever in this specification the terms ending in "itan" and "ide" are employed, that these terms do not necessarily describe a single chemical compound but may refer to a mixture of several anhydro derivatives falling therein. Thus, in the case of sugar alcohol substrates, glycitan is not necessarily a single mono-anhydroglycitol but may comprise several isomeric mono-anhydroglycitols.

The unsaturated fatty acids employed in the method described herein are products of a metathesis process. Non-limiting examples of procedures for making hydrocarbyl unsaturated fatty acids and esters by metathesis are disclosed in WO 2008/048522, the contents of which in their entirety are specific incorporated herein by reference. In particular, Examples 8 and 9 of WO 2008/048522 may be employed to produce methyl 9-decenoate and methyl 9-dodecenoate, hydrolysis precursors for 9-decenoic acid and 9-dodecenoic acid. Suitable procedures also appear in U.S. Pat. Appl. Publ. No. 2011/0113679, the teachings of which in their entirety are also incorporated herein by reference.

Preferably, at least a portion of the metathesis-derived hydrocarbyl unsaturated fatty acids have "Δ9" unsaturation, that is, the carbon-carbon double bond in the acid exists at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-Δ9, preferably at least 25 mole % trans-Δ9, more preferably at least 50 mole % trans-Δ9, and even more preferably at least 80% trans-Δ9. The unsaturation may be greater than 90 mole %, greater than 95 mole %, or even 100% trans-Δ9. In contrast, naturally sourced fatty acids that have Δ9 unsaturation, e.g., oleic acid, usually have ~100% cis-isomers.

Although a high proportion of trans-geometry (particularly trans-Δ9 geometry) may be desirable in the metathesis-derived unsaturated fatty acid employed in the method described herein, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal., A* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-Δ9 geometry.

An elevated proportion of trans-isomer content, relative to the usual predominantly or all-cis configuration of the conventionally derived hydrocarbyl unsaturated fatty acid, imparts different physical properties to the metathesis-derived unsaturated fatty acid and to the metathesis-derived unsaturated glycitan fatty esters produced from them. These physical property differences include, for example, modified physical form, melting range, compactability, and other important properties. These differences allow formulators that use the unsaturated glycitan fatty esters produced by the method described herein greater latitude or expanded choice as they use them in cleaners, detergents, personal care, agricultural uses, specialty foams, and other end uses.

Unsaturation in the alkenyl moiety of the unsaturated glycitan fatty esters can also impart advantages not seen in the saturated counterparts. For example, unsaturated glycitan fatty esters have lower melting points than do their saturated counterparts, which therefore reduce liquid crystal formation in their aqueous solutions. Unsaturated glycitan fatty esters are also more soluble in organic solvents and in their aqueous solutions, and therefore exhibit higher critical micelle concentration values, relative to their analogous saturated counterparts. Moreover, unsaturated fatty esters of glycitans display relatively lower inherent viscosities both free of solvent and in their aqueous solutions than do their analogous saturated counterparts. By contrast to aqueous solutions of glycitan fatty esters prepared from conventionally sourced saturated fatty acids, aqueous solutions of unsaturated glycitan fatty esters display distinct liquid polymorphism behavior over the broad range of surfactant concentrations employed. This distinctive performance can be rationalized on the basis of differences between the micelle structures of unsaturated glycitan fatty esters and glycitan fatty esters prepared from conventionally sourced fatty acids. Also, unsaturation in the alkenyl moiety of the unsaturated glycitan fatty esters affects the hydrophilic/lipophilic balance value which can have a positive impact on its cleaning, emulsification, and dispersancy properties. Because crystallinity is disrupted by the presence of a carbon-carbon double bond, unsaturated glycitan fatty esters can be concentrated and formulated at higher active levels—sometimes much higher—than their saturated counterparts. Thus, the seemingly minor structural change to an unsaturated product can enable shipment of more concentrated products, reduce or eliminate the need for special handling equipment, and/or ultimately provide substantial cost savings.

The starting composition of the metathesis process comprises an unsaturated fatty acid or unsaturated fatty ester or a mixture thereof. As used herein the terms "unsaturated fatty acid" "hydrocarbyl unsaturated fatty ester" refer to compounds that have an alkene chain with a terminal carboxylic acid group. The alkene chain may be a linear or branched and may optionally include one or more functional groups in addition to the carboxylic acid group. For example, some carboxylic acids include one or more hydroxyl groups. The alkene chain typically contains about 4 to about 30 carbon atoms, more typically about 4 to about 22 carbon atoms. In many embodiments, the alkene chain contains 18 carbon atoms (i.e., a C18 fatty acid). The unsaturated fatty acids have at least one carbon-carbon double bond in the alkene chain (i.e., a monounsaturated fatty acid), and may have more than one double bond (i.e., a polyunsaturated fatty acid) in the alkene chain. In exemplary embodiments, the unsaturated fatty acids have from 1 to 3 carbon-carbon double bonds in the alkene chain.

Also useful as starting compositions of the metathesis process are unsaturated fatty esters. As used herein the term "unsaturated fatty ester" refers to a compound that has an alkene chain with a terminal ester group. The alkene chain may be linear or branched and may optionally include one or more functional groups in addition to the ester group. For example, some unsaturated fatty esters include one or more hydroxyl groups in addition to the ester group. Unsaturated fatty esters include "unsaturated monoesters" and "unsaturated polyol esters". Unsaturated monoesters have an alkene chain that terminates in an ester group, for example, an alkyl ester group such as a methyl ester. The alkene chain of the unsaturated monoesters typically contains about 4 to about 30 carbon atoms, more typically about 4 to 22 carbon atoms. In exemplary embodiments, the alkene chain contains 18 carbon atoms (i.e., a C18 fatty ester). The unsaturated monoesters have at least one carbon-carbon double bond in the alkene chain and may have more than one double bond in the alkene chain. In exemplary embodiments, the unsaturated fatty ester has 1 to 3 carbon-carbon double bonds in the alkene chain.

In many embodiments, the unsaturated fatty acid or ester has a straight alkene chain and can be represented by the general formula:

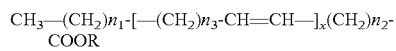

where: R is hydrogen (fatty acid), an aliphatic group (fatty ester), or a metal ion (carboxylate salt); n1 is an integer equal to or greater than 0 (typically 0 to 15; more typically 0, 3, or 6); n2 is an integer equal to or greater than 0 (typically 2 to 11; more typically 3, 4, 7, 9, or 11); n3 is an integer equal to or greater than 0 (typically 0 to 6; more typically 1); and x is an integer equal to or greater than 1 (typically 1 to 6, more typically 1 to 3). A summary of some suitable fatty acids and fatty esters is presented in Table A of published U.S. Patent Application No. 2009/0264672A1, which published patent application in its entirety is specifically incorporated herein by reference.

Suitable unsaturated monoesters include alkyl esters (e.g., methyl esters) or aryl esters and may be derived from unsaturated fatty acids or unsaturated glycerides by transesterifying with a monohydric alcohol. The monohydric alcohol may be any monohydric alcohol that is capable of reacting with the unsaturated free fatty acid or unsaturated glyceride to form the corresponding unsaturated monoester. In some embodiments, the monohydric alcohol is a C1 to C20 monohydric alcohol, for example, a C1 to C12 monohydric alcohol, a C1 to C8 monohydric alcohol, or a C1 to C4 monohydric alcohol. The carbon atoms of the monohydric alcohol may be arranged in a straight chain or in a branched chain structure, and may be substituted with one or more substituents. Representative examples of monohydric alcohols include methanol, ethanol, propanol (e.g., isopropanol), and butanol.

Transesterification of an unsaturated triglyceride can be represented as follows.

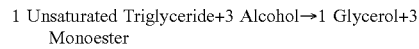

Depending upon the make-up of the unsaturated triglyceride, the above reaction may yield one, two, or three moles of unsaturated monoester. Transesterification is typically conducted in the presence of a catalyst, for example, alkali catalysts, acid catalysts, or enzymes. Representative alkali transesterification catalysts include NaOH, KOH, sodium and potassium alkoxides (e.g., sodium methoxide), sodium ethoxide, sodium propoxide, and sodium butoxide. Representative acid catalysts include sulfuric acid, phosphoric acid, hydrochloric acid, and sulfonic acids. Heterogeneous catalysts may also be used for transesterification. These include alkaline earth metals or their salts such as CaO, MgO, calcium acetate, barium acetate, natural clays, zeolites, Sn, Ge or Pb, supported on various materials such as ZnO, MgO, $TiO_2$, activated carbon or graphite, and inorganic oxides such as alumina, silica-alumina, boria, oxides of P, Ti, Zr, Cr, Zn, Mg, Ca, and Fe. In exemplary embodiments, the triglyceride is transesterified with methanol in order to form free fatty acid methyl esters.

In some embodiments, the unsaturated fatty esters are unsaturated polyol esters. As used herein the term "unsaturated polyol ester" refers to compounds that have at least one unsaturated fatty acid that is esterified to the hydroxyl group of a polyol. The other hydroxyl groups of the polyol may be unreacted, or may be esterified with a saturated or unsaturated fatty acid. The fatty acids in the polyol ester may be linear or branched and may optionally have functional groups other than the carboxylic acid such as one or more hydroxyl groups. Examples of polyols include glycerol, 1,3-propanediol, propylene glycol, erythritol, trimethylolpropane, pentaerythritol, and sorbitol.

In many embodiments, unsaturated polyol esters have the general formula:

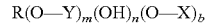

where R is an organic group having a valency of (n+m+b); m is an integer from 0 to (n+m+b−1), typically 0 to 2; b is an integer from 1 to (n+m+b), typically 1 to 3; n is an integer from 0 to (n+m+b−1), typically 0 to 2; (n+m+b) is an integer that is 2 or greater; X is —(O)C—(CH$_2$)$_{n2}$—[—CH=CH—(CH$_2$)$_{n3}$-]$_x$—(CH$_2$)$_{n1}$—CH$_3$; Y is —(O)C—R'; R' is a straight or branched chain alkyl or alkenyl group; n$_1$ is an integer equal to or greater than 0 (typically 0 to 15; more typically 0, 3, or 6); n$_2$ is an integer equal to or greater than 0 (typically 2 to 11; more typically 3, 4, 7, 9, or 11); n$_3$ is an integer equal to or greater than 0 (typically 0 to 6; more typically 1); and x is an integer equal to or greater than 1 (typically 1 to 6, more typically 1 to 3).

In many embodiments, the unsaturated polyol esters are unsaturated glycerides. As used herein the term "unsaturated glyceride" refers to a polyol ester having at least one (e.g., 1 to 3) unsaturated fatty acid that is esterified with a molecule of glycerol. The fatty acid groups may be linear or branched and may include pendant hydroxyl groups. In many embodiments, the unsaturated glycerides are represented by the general formula:

ACH$_2$—CHB—CH$_2$C where -A; -B; and -C are selected from —OH; —O(O)C—(CH$_2$)$_{n2}$—[—CH=CH—(CH$_2$)$_{n3}$—]—(C—H$_2$)$_{n1}$—CH$_3$; and —O(O)C—R'; with the proviso that at least one of -A, -B, or -C is —O(O)C—(CH$_2$)$_{n2}$—[—CH=CH—(CH$_2$)$_{n3}$—]—(CH$_2$)$_{n1}$—CH$_3$. In the above formula: R' is a straight or branched chain alkyl or alkenyl group; n$_1$ is an integer equal to or greater than 0 (typically 0 to 15; more typically 0, 3, or 6); n$_2$ is an integer equal to or greater than 0 (typically 2 to 11; more typically 3, 4, 7, 9, or 11); n$_3$ is an integer equal to or greater than 0 (typically 0 to 6; more typically 1); and x is an integer equal to or greater than 1 (typically 1 to 6, more typically 1 to 3).

As shown in the formula above, the unsaturated glyceride may include monounsaturated fatty acids, polyunsaturated fatty acids, and saturated fatty acids that are esterified to the glycerol molecule. The main chain of the individual fatty acids may have the same or different chain lengths. Accordingly, the unsaturated glyceride may contain up to three different fatty acids so long as at least one fatty acid is an unsaturated fatty acid. Unsaturated glycerides having two —OH groups (e.g., -A and -B are —OH) are commonly known as unsaturated monoglycerides. Unsaturated glycerides having one —OH group are commonly known as unsaturated diglycerides. Unsaturated glycerides having no —OH groups are commonly known as unsaturated triglycerides.

In many embodiments, useful starting compositions are derived from natural oils such as plant-based oils or animal fats. Representative examples of plant-based oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, castor oil, and the like. Representative examples of animal fats include lard, tallow, chicken fat (yellow grease), and fish oil. Other useful oils include tall oil and algae oil.

In many embodiments, the plant-based oil is soybean oil. Soybean oil comprises unsaturated glycerides, for example, in many embodiments about 95% weight or greater (e.g., 99% weight or greater) triglycerides. Major fatty acids making up soybean oil include saturated fatty acids, for example, palmitic acid (hexadecanoic acid) and stearic acid (octadecanoic acid), and unsaturated fatty acids, for example, oleic acid (9-octadecenoic acid), linoleic acid (9,12-octadecadienoic acid), and linolenic acid (9,12,15-octadecatrienoic acid). Soybean oil is a highly unsaturated vegetable oil with many of the triglyceride molecules having at least two unsaturated fatty acids.

This metathesis process can be used to produce multiple organic acid compounds. As discussed below, the position of the carbon-carbon double bond closest to the carboxylic acid or carboxylic acid ester group dictates the chain length of the organic acid compound that is formed by the method described herein. In a preferred embodiment, the starting composition of the metathesis process comprises a Δ9 unsaturated fatty acid, a Δ9 unsaturated fatty ester (e.g., monoesters or polyol esters), or a mixture thereof. Δ9 unsaturated starting materials have a carbon-carbon double bond located between the 9th and 10th carbon atoms (i.e., between C9 and C10) in the alkene chain of the unsaturated fatty acid or ester. In determining this position, the alkene chain is numbered beginning with the carbon atom in the carbonyl group of the unsaturated fatty acid or ester. Δ9 unsaturated fatty acids, esters, and salts include polyunsaturated fatty acids, esters, or salts (i.e., having more than one carbon-carbon double bond in the alkene chain) so long as one of the carbon-carbon double bonds is located between C9 and C10. For example, included within the definition of Δ9 unsaturated fatty acids or esters are Δ9, 12 unsaturated fatty acids or esters, and Δ9, 12, 15 unsaturated fatty acids or esters.

In many embodiments, the Δ9 unsaturated starting materials have a straight alkene chain and may be represented by the general structure:

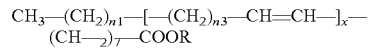

CH$_3$—(CH$_2$)$_{n1}$—[—(CH$_2$)$_{n3}$—CH=CH—]$_x$—(CH$_2$)$_7$—COOR where R is hydrogen (fatty acid), an aliphatic group (fatty monoester) or a metal ion (carboxylate salt); n1 is an integer equal to or greater than 0 (typically 0 to 6; more typically 0, 3, 6); n3 is an integer equal to or greater than 0 (typically 1); and x is an integer equal to or greater than 1 (typically 1 to 6, more typically 1 to 3).

In exemplary embodiments, the Δ9 unsaturated starting materials have a total of 18 carbons in the alkene chain. Examples include

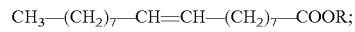

CH$_3$—(CH$_2$)$_7$—CH=CH—(CH$_2$)$_7$—COOR;

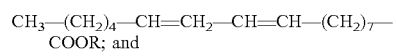

CH$_3$—(CH$_2$)$_4$—CH=CH—CH$_2$—CH=CH—(CH$_2$)$_7$—COOR; and

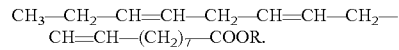

CH$_3$—CH$_2$—CH=CH—CH$_2$—CH=CH—CH$_2$—CH=CH—(CH$_2$)$_7$—COOR.

where R is hydrogen (fatty acid) or an aliphatic group (fatty monoester);

Δ9 unsaturated fatty esters may be monoesters or polyol esters. In many embodiments, the Δ9 unsaturated polyol esters have the general structure

ACH$_2$—CHB—CH$_2$C where -A; -B; and -C are independently selected from —OH; —O(O)C—R'; and —O(O)C—(CH$_2$)$_7$—[—CH=CH—(CH$_2$)$_{n3}$—]$_x$—(CH$_2$)$_{n1}$—CH$_3$; with the proviso that at least one of -A, -B, or -C is —O(O)C—(CH$_2$)$_7$—[—CH=CH—(CH$_2$)$_{n3}$—]$_x$—(CH$_2$)$_{n1}$—CH$_3$. In the above formula: R' is a straight or branched chain alkyl or alkenyl group; n$_1$ is an integer equal to or greater than 0 (typically 0 to 6; more typically 0, 3, 6); n3 is an integer equal to or greater than 0 (typically 1); and x is an integer equal to or greater than 1 (typically 1 to 6, more typically 1 to 3).

In exemplary embodiments, the starting composition of the metathesis process comprises one or more C18 fatty acids, for example, oleic acid (i.e., 9-octadecenoic acid), linoleic acid (i.e., 9,12-octadecadienoic acid), and linolenic acid (i.e., 9,12,15-octadecatrienoic acid). In other exemplary embodiments, the starting composition comprises one or more C18 fatty esters, for example, methyl oleate, methyl linoleate, and methyl linolenate. In yet another exemplary embodiment, the starting composition comprises an unsaturated glyceride comprising Δ9 fatty acids, for example, C18 Δ9 fatty acids.

Δ9 starting compositions of the metathesis process may be derived, for example, from vegetable oils such as soybean oil, rapeseed oil, corn oil, sesame oil, cottonseed oil, sunflower oil, canola oil, safflower oil, palm oil, palm kernel oil, linseed oil, castor oil, olive oil, peanut oil, and the like. Since these vegetable oils yield predominately in glyceride form, the oils are typically processed (e.g., by transesterification) to yield unsaturated free fatty esters, unsaturated free fatty acids, or carboxylate salts thereof. Δ9 starting materials may also be derived from tung oil which typically contains oleic acid, linoleic acid, and eleostearic acid (C18; Δ9, 11, 13) in glyceride form. Δ9 starting materials may also be derived from tall oil, fish oil, lard, and tallow.

The starting composition for the metathesis process is cross-metathesized with a short-chain olefin in the presence of a first metathesis catalyst in a first metathesis step to form cross-metathesis products comprising: (i) one or more olefin compounds; and (ii) one or more monocarboxylic fatty acid- or ester-functionalized alkenes having at least one carbon-carbon double bond. This monocarboxylic fatty acid or ester can be used to react with intramolecular condensates of glycitols having four or more carbons in the method described herein to produce unsaturated fatty glycitan esters.

Short-chain olefins are short chain length organic compounds that have at least one carbon-carbon double bond. In many embodiments, the short chain olefins have between about 4 and about 9 carbon atoms. Short chain olefins can be represented by the structure:

where $R^7$, $R^8$, $R^{9'}$ and $R^{10}$ are each, independently, hydrogen, or an organic group, with the proviso that at least one of $R^7$ or $R^8$, is an organic group. The organic group may be an aliphatic group, an alicyclic group, or an aromatic group. Organic groups may optionally include heteroatoms (e.g., O, N, or S atoms), as well as functional groups (e.g., carbonyl groups). The term aliphatic group means a saturated or unsaturated, linear or branched, hydrocarbon group. This term is used to encompass alkyl groups. The term alkyl group means a monovalent, saturated, linear, branched, or cyclic hydrocarbon group. Representative examples of alkyl groups include methyl, ethyl, propyl (n-propyl or i-propyl), butyl (n-butyl or t-butyl), pentyl, hexyl, and heptyl. An alicyclic group is an aliphatic group arranged in one or more closed ring structures. The term is used to encompass saturated (i.e., cycloparaffins) or unsaturated (cycloolefins or cycloacetylenes) groups. An aromatic or aryl group is an unsaturated cyclic hydrocarbon having a conjugated ring structure. Included within aromatic or aryl groups are those possessing both an aromatic ring structure and an aliphatic or alicyclic group. When $R^8$, $R^9$, and $R^{10}$ are each hydrogen, the short-chain olefin is an alpha olefin, such as 1-propene, 1-butane, 1-pentene, 1-hexene, 1-octene, and 1-nonene.

In many embodiments, the short-chain olefin is a short-chain internal olefin. Short-chain internal olefins may be represented by the structure:

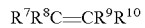

where $R^7$, $R^8$, $R^9$, and $R^{10}$ are each, independently, hydrogen or an organic group, with the proviso that at least one of $R^7$ or $R^8$ is an organic group, and at least one of $R^9$, or $R^{10}$ is an organic group. Short-chain internal olefins may be symmetric or asymmetric. Symmetric short-chain internal olefins having one carbon-carbon double bond may be represented by the structure:

where $R^7$ and $R^9$ are same organic group. Representative examples of symmetric short-chain internal olefins include 2-butene, 3-hexene, and 4-octene. In some embodiments, the short-chain internal olefin is asymmetric. Representative examples of asymmetric short-chain internal olefins include 2-pentene, 2-hexene, 2-heptene, 3-heptene, 2-octene, 3-octene, 2-nonene, 3-nonene, and 4-nonene.

In many embodiments, symmetric short-chain internal olefins are preferred for cross-metathesis because the cross-metathesis products that result will include fewer products than if an asymmetric short-chain internal olefin is used for cross-metathesis. For example, as shown below, when a first double-bond containing compound (i.e., A=B) is cross-metathesized with a symmetric short-chain internal olefin (i.e., represented by C=C), two cross-metathesis products are produced. By contrast, when the same double-bond containing compound is cross-metathesized with an asymmetric short-chain internal olefin (i.e., represented by C=D), four cross-metathesis products are produced. Cross-metathesis of symmetric short-chain internal olefin (C=C) reacts as follows:

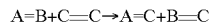

Cross-metathesis of asymmetric short-chain internal olefin

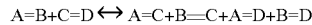

The aforesaid unsaturated fatty acid, unsaturated fatty ester, or unsaturated fatty acid salt undergoes metathesis with an aforesaid short-chain olefin in the presence of a catalytically effective amount of a metathesis catalyst. The term "metathesis catalyst" includes any catalyst or catalyst system which catalyzes the olefin metathesis reaction. Any known or future-developed metathesis catalyst may be used, alone or in combination with one or more additional catalysts. Exemplary metathesis catalysts include metal carbene catalysts based upon transition metals, for example, ruthenium, molybdenum, osmium, chromium, rhenium, and tungsten.

Suitable homogeneous metathesis catalysts for use as the first metathesis catalyst in the first metathesis step include combinations of a transition metal halide or oxo-halide (e.g., WOCl$_4$ or WCl$_6$) with an alkylating cocatalyst (e.g., Me$_4$Sn). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

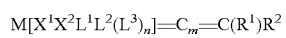

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α, β-, or γ- with respect to the carbene carbon to provide the bidentate ligand. Examples of suitable Grubbs-Hoveyda catalysts appear in the '086 publication.

Heterogeneous catalysts suitable for use in the first metathesis catalyst in the first metathesis step include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin, lead, germanium, or silicon compound. Others include $MoCl_3$ or $MoCl_5$ on silica activated by tetraalkyltins.

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica, or alumina. Such an immobilized catalyst may be used in a flow process. An immobilized catalyst can simplify purification of products and recovery of the catalyst so that recycling the catalyst may be more convenient.

As is understood in the field of catalysis, suitable solid supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

The metathesis process can be conducted under any conditions adequate to produce the desired metathesis product or products. For example, stoichiometry, atmosphere, solvent, temperature and pressure can be selected to produce a desired product and to minimize undesirable byproducts. The metathesis process may be conducted under an inert atmosphere. Similarly, if an olefin reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen, and combinations thereof.

Similarly, if a solvent is used, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Using currently known catalysts, the processing temperature in the first metathesis step may largely be a rate-dependent variable where the temperature is selected to provide a desired product at an acceptable production rate. The selected temperature may be greater than about −40° C., may be more than about −20° C., and is generally selected to be more than about 0° C. or more than about 20° C. Generally, the process temperature may be no more than about 150° C., and may be no more than about 120° C. Thus, an exemplary temperature range for the reaction in the first metathesis step may be from about 20° C. to about 120° C. Lower temperatures can be used, for example, to minimize the production of undesired impurities or to favor a particular reaction pathway.

Any useful amount of the selected first metathesis catalyst can be used in the first metathesis step. For example, the molar ratio of the unsaturated polyol ester to catalyst may range from about 5:1 to about 10,000,000:1 or from about 50:1 to 500,000:1.

The first metathesis step can be conducted under any desired pressure. For example, it is typically conducted at a pressure ranging from about 10 kPa to about 7000 kPa or from about 100 kPa to about 3000 kPa. In some embodiments, it is preferred to conduct the first metathesis step at low pressure, for example, about 0.01 kPa to about 100 kPa, more typically about 0.01 kPa to about 50 kPa. By conducting the first metathesis at low pressure, the low boiling point olefin products (e.g., the short-chain internal olefin or alpha olefin) that are formed during the reaction can be easily separated from the higher boiling point functionalized olefin products (e.g., the one or more diacid olefins, diester olefins, or disalt olefins). This separation of the short-chain internal olefin product allows this material to be recycled back to the reactor where the cross-metathesis step is being conducted.

The mixture of cross-metathesis products comprises at least one of a monocarboxylic unsaturated fatty acid or a monocarboxylic unsaturated fatty ester, at least a portion of which is then separated from the remaining cross-metathesis products. This allows the separation step to separate the monocarboxylic unsaturated fatty acid or monocarboxylic unsaturated fatty ester from any analogous alkane that may be present in the cross-metathesis products.

Useful techniques for separating the monocarboxylic unsaturated fatty acid or monocarboxylic unsaturated fatty ester from the remaining cross-metathesis products include, for example, distillation, reactive distillation, chromatography, fractional crystallization, membrane separation, liquid/liquid extraction, or a combination thereof.

In many embodiments, the monocarboxylic unsaturated fatty acid or monocarboxylic unsaturated fatty ester may be purified to a high degree using one or more of the above-described techniques. For example, the monocarboxylic unsaturated fatty ester can be purified to a level of 90% wt. or greater (e.g., 95% wt. or greater, 96% wt. or greater, 97% wt. or greater, 98% wt. or greater, 99% wt. or greater, 99.5% wt. or greater, or 99.9% wt. or greater). Thus, a high purity monocarboxylic unsaturated fatty acid and monocarboxylic unsaturated fatty ester can be obtained using one or more conventional separation processes.

Achieving such a high purity allows for the production of a high purity unsaturated fatty glycitan esters formed by the reaction of intramolecular condensates of glycitols having four or more carbons with a monocarboxylic unsaturated fatty acid in the method described herein. For example, in some embodiments, the unsaturated fatty acid produced has a purity of 90% wt. or greater (e.g., 95% wt. or greater, 96% wt. or greater, 97% wt. or greater, 98% wt. or greater, 99% wt. or greater, 99.5% wt. or greater, or 99.9% wt. or greater).

If an intramolecular condensate of a glycitol having four or more carbons is to be reacted with a dicarboxylic unsaturated fatty acid in the method described herein, then after the aforesaid separation, the isolated monocarboxylic unsaturated fatty acid or monocarboxylic unsaturated fatty ester is reacted in the second metathesis step of either self-metathesis or cross-metathesis with a second acid- or ester-functionalized alkene in the presence of a second metathesis catalyst.

When the monocarboxylic unsaturated fatty acid or monocarboxylic unsaturated fatty ester is self-metathesized in the presence of the second metathesis catalyst, a composition comprising one or more unsaturated dicarboxylic acids or unsaturated dicarboxylic esters is produced. For example, when a Δ9 acid-functionalized starting composition is used and is cross-metathesized with 2-butene, the resulting acid-functionalized alkene has the structure HOOC—(CH$_2$)$_7$—CH=CH—CH$_3$. After separation, self-metathesis of the acid-functionalized alkene yields an unsaturated C18 diacid and 2-butene according to the formula below:

2HOOC—(CH$_2$)$_7$—CH=CH—CH$_3$→

HOOC—(CH$_2$)$_7$CH=CH—(CH$_2$)$_7$—COOH+H$_3$C—CH=CHCH$_3$

In similar fashion, when a Δ9 methyl ester-functionalized starting composition is used and is cross-metathesized with 2-butene, the resulting methyl ester-functionalized alkene has structure CH$_3$OOC—(CH$_2$)$_7$—CH=CH—CH$_3$. Self-metathesis of the ester-functionalized olefin yields an unsaturated C18 diester and 2-butene according to the formula below:

2CH$_3$OOC—(CH$_2$)$_7$—CH=CH—CH$_3$→CH$_3$OOC—(CH$_2$)$_7$—CH=CH—(CH$_2$)$_7$—COOCH$_3$+H$_3$C—CH=CH—CH$_3$

In the alternative, when the monocarboxylic unsaturated fatty acid or monocarboxylic unsaturated fatty ester is cross-metathesized with a second functionalized alkene compound in the presence of the second metathesis catalyst in the second metathesis step, a bifunctional organic compound is formed. Exemplary bifunctional organic compounds obtainable by this method include diacids, diesters or mixed acid/ester species. The second functionalized alkene compound has at least one carbon-carbon double bond and has at least two carboxylic acids or carboxylic esters as the functional groups. In many embodiments, the second functionalized alkene has the general structure:

R$^{12}$—CH=CH—(CH$^2$)$_n$—R$^{13}$ where n is 0 or an integer (typically 1 to 20); —R$^{12}$ is hydrogen, an alkyl group, an aryl group, or —(CH$_2$)$_n$—R$^{13}$; —R$^{13}$ is a functional group (typically —COOH, —COOR$^{14}$, or —COOX; —R$^{14}$ is alkyl group or an aryl group; and —X is a metal.

Examples of second functionalized alkene compounds include 2-butene-1,4-dioic acid, acrylic acid, 2-butenoic acid, 2-pentenoic acid, 2-hexenoic acid, 3-hexenedioc acid, the dimethyl ester of 3-hexenedioc acid 3-hexenoic acid, the methyl ester of 3-hexenoic acid, 3-pentenoic acid, methyl ester of 3-pentenoic acid, 4-pentenoic acid, 4-hexenoic acid, 4-heptenoic acid, 4-octenoic acid and its esters, 4-octene-1,8-dioic acid and its esters, 5-hexenoic acid, 5-heptenoic acid, 5-octenoic acid and its esters, 5-decene-1,10-dioic acid and its esters, 6-heptenoic acid, 6-octenoic acid, 6-nonenoic acid, 6-decenoic acid and its esters, 6-dodecene-1,12-dioic acid and its esters, 7-octenoic acid, 7-nonenoic acid, 7-decenoic acid, 7-undecenoic acid, and 7-dodecenoic acid and its esters.

In exemplary embodiments, the second functionalized alkene is symmetric about its carbon-carbon double bond. That is, the group —R$_{12}$ is the same as group —(CH$_2$)$_n$—R$^{13}$. Advantageously, when the second functionalized alkene is symmetric, the number of products formed in the second metathesis step is reduced as compared to cross-metathesis reactions where the second functionalized alkene is asymmetric. This may provide for higher yields and/or easier separation of the desired bifunctional compound. Representative examples of symmetric functionalized alkenes include maleic acid and esters thereof, 3-hexenedioc acid and esters and acids salts thereof (e.g., the dimethyl ester of 3-hexenedioc acid), 4-octene-1,8-dioic acid and esters and acids salts thereof, 5-decene-1,10-dioic acid and esters and acids salts thereof, and 6-dodecene-1,12-dioic acid esters.

In an exemplary embodiment, a Δ9 acid-functionalized starting composition is used and is cross-metathesized with 2-butene in the first metathesis step, providing an acid-functionalized alkene having the structure HO$_2$C—(CH$_2$)$_7$—CH=CH—CH$_3$. After separation, the acid-functionalized alkene is cross-metathesized with 3-hexenedioc acid in the second metathesis step. The second metathesis step in the two-step metathesis process yields an unsaturated C12 diacid according to the formula below:

HO$_2$C—(CH$_2$)$_7$—CH=CH—CH$_3$+
HO$_2$CCH$_2$CH=C—HCH$_2$COH→HO$_2$C—
(CH$_2$)$_7$CH=CH—CH$_2$—CO$_2$H+CH$_3$-
CH=CHCH$_2$CO$_2$H

In another exemplary embodiment, a Δ9 acid-functionalized starting composition is used and is cross-metathesized with 2-butene in the first metathesis step, providing an acid-functionalized alkene having the structure HO$_2$C—(CH$_2$)$_7$—CH=CH—CH$_3$. After separation, the acid-functionalized alkene is cross-metathesized with maleic acid (HO$_2$C—CH=CH—CO$_2$H) in the second metathesis step. The second metathesis step in the two-step metathesis process yields an unsaturated C11 diacid according to the formula below:

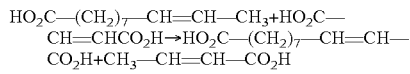

Compositions and the amounts thereof described hereinabove that are suitable for use for the first metathesis catalyst in the first metathesis step are also suitable for use for the second metathesis catalyst in the second metathesis step. The second metathesis catalyst can be the same as or different from the first metathesis catalyst. The temperature and pressure employed in the second metathesis step are within the ranges for temperature and pressure, respectively, described hereinabove for the first metathesis step.

The monocarboxylic unsaturated fatty acids produced in the second metathesis step are suitable to react with the intramolecular condensates of glycitols having four or more carbons to produce unsaturated glycitan fatty esters.

Suitable metatheses-derived unsaturated fatty acids have the formula

where $R^{16}$ is hydrogen, an alkyl group, an aryl group or (CH$_2$)$_7$—$R^{17}$; $R^{17}$ is —COOH; and m is an integer from 1 to 20.

The metathesis-derived unsaturated fatty acid employed in the method described herein can be either monocarboxylic, in which case $R^{16}$ above is hydrogen, an alkyl group, or an aryl group, or dicarboxylic in which case $R^{16}$ is —COOH. The monocarboxylic unsaturated fatty acid is the product of the first metathesis step described hereinabove, and the dicarboxylic unsaturated fatty acid is the product of the second metathesis step described hereinabove. The metathesis-derived unsaturated fatty acids employed preferably are 9-decenoic acid, 9-dodecenoic acid, 9-tridecenoic acid, 9-pentadecenoic acid, 9-octodecenoic acid, and 9-octadecene-1,18-dioic acid and more preferably are 9-decenoic acid, 9-dodecenoic acid and 9-octodecene-1,18-dioic acid. 9-decenoic acid, 9-dodecenoic acid, 9-tridecenoic acid, 9-pentadecenoic acid, and 9-octadecenoic acid, and 9-octadecen-1,18-dioic acid, which are not metathesis-derived, can be substituted for their metathesis-derived counterparts in the method described herein, but in that case the benefit of a high trans-isomers content is not obtained.

As indicated hereinabove, methods are described for the preparation of unsaturated glycitan fatty esters, the glycitans of which are prepared via the intramolecular condensation reaction of glycitols having four or more carbons. Glycitols preferred for the preparation of unsaturated glycitan fatty esters are sorbitol, xylitol, mannitol and dulcitol; more preferred are sorbitol, xylitol and mannitol; most preferred for the preparation of an unsaturated glycitan fatty ester is sorbitol. Solely for the purpose of convenience herein, the method described herein for the preparation of an unsaturated glycitan fatty ester shall be illustrated and described in terms of the preparation of an unsaturated fatty ester of sorbitol.

When preparing an unsaturated fatty ester of sorbitol, it is important to prepare anhydro sorbitol or "sorbitan" first and then in a separate step to react this anhydro sorbitol or "sorbitan" with a mono- or dicarboxylic fatty acid at a temperature not exceeding about 215° C. in the presence of a n alkaline catalyst in order to produce the desired sorbitan fatty ester. It is important to use temperatures not exceeding 215° C. in order to avoid the color formation which has characterized sorbitan esters prepared by conventional methods. It is essential to carry out anhydridization (the process of intramolecular condensation) and esterification as separate steps, rather than as a single step, in order to meet product specifications such as hydroxyl number, acid number, and saponification number. Fatty acid esterification of sorbitol rather than sorbitan at temperatures below 215° C. in the presence of a basic catalyst results in products which do not meet established specifications for sorbitan fatty ester surfactants.

In the preliminary step sorbitol is anhydridized in the presence of an alkaline or acid catalyst until an anhydro sorbitol having the desired degree of anhydridization is obtained. The degree of anhydridization can be determined by measuring the hydroxyl number of a sample according to known techniques. Pure sorbitol, for example, has a hydroxyl number of 1850. An anhydro sorbitol (i.e., sorbitan) from which an average of 1.0 mole of water has been chemically removed for each mole of sorbitol initially present, has a hydroxyl value of 1368. Broadly, the hydroxyl number of the anhydro sorbitol should be in the range from about 1150 to about 1400, which represents a range from about 1.0 to approximately 1.4, in the degree of anhydridization. More specifically, in the method described herein, the desired degree of anhydridization for the anhydro sorbitol depends both on a mono- or dicarboxylic fatty acid or ester and the temperature to be used in esterification. For example, the desired anhydro sorbitol for making a sorbitan 9-dodecenoate surfactant has a hydroxyl number in the range of about 1150 to about 1250, while the desired anhydro sorbitol for making a sorbitan 9-octadecenoate surfactant has a hydroxyl number in the range of about 1250 to about 1400. In each case, an anhydro sorbitol having a hydroxyl value toward the higher end of the range is chosen when an esterification temperature close to 215° C. is to be used, and an anhydro sorbitol having a lower hydroxyl value within the range is chosen when lower esterification temperatures are to be used.

The preparation of sorbitan from sorbitol is preferably carried out at temperatures of from about 90° C., preferably 110° C., to about 130° C., preferably to about 120° C., and at reduced pressure (e.g., 5 or 5-40 mmHg), in the presence of p-toluenesulfonic acid as the acid catalyst. The reaction is continued until a product having the desired hydroxyl number is reached. It is understood that other acid catalysts and conditions can be used. It is preferred to carry out the anhydridization in the presence of decolorizing carbon. The degree of anhydridization may be controlled by controlling the reaction time. When conducting the intramolecular dehydration of sorbitol at 120° C. and at 5 mm of mercury absolute, the reaction time is about 70 minutes when a product having a hydroxyl number of about 1300 is desired, and about 110 minutes when a product having the hydroxyl number of about 1200 is desired. Alternatively the degree of anhydridization may be controlled by choice of reaction temperature, pressure, acid catalyst, catalyst concentration, or a combination of these parameters. An increase in temperature, catalyst concentration, or the strength of the acid catalyst, or a decrease in absolute pressure, increases the degree of anhydridization.

The anhydro sorbitol employed in the method described herein is typically a mixture of sorbitans, i.e., 1,4-sorbitan, 2,5-sorbitan, and 3,6-sorbitan, with small amounts of isosorbide and unreacted sorbitol; 1,4-sorbitan is the largest constituent of the anhydro sorbitol. Anhydro sorbitol, having a hydroxyl number from about 1150 to about 1400 and preferably prepared as described above, is reacted with an aforesaid metathesis-derived unsaturated mono- or dicarboxylic fatty acid in the presence of a base at a temperature not exceeding about 215° C. in order to make the desired unsaturated sorbitan fatty ester. The reaction is carried out by heating the anhydro sorbitol, an aforesaid mono- or dicarboxylic fatty acid alkaline catalyst, and decolorizing carbon (when used) together, preferably in an inert (e.g., nitrogen) atmosphere until the desired reaction temperature is reached and maintaining this temperature for a sufficient length of time to obtain the desired product. The aforesaid mono- or dicarboxylic unsaturated fatty acids may contain from about 8 to about 30 carbon atoms, although the naturally occurring materials containing from 10 to 18 carbon atoms are preferred. The aforesaid mono- or dicarboxylic unsaturated fatty acids need not be pure chemical compounds. The amount of mono- or dicarboxylic unsaturated fatty acid used is usually in excess of the stoichiometric quantity required for formation of the desired product. In some embodiments, the mole ratio of metathesis-derived unsaturated fatty acid to sorbitol varies from about 1.1 when sorbitan 9-dodecenoate is being prepared to about 1.33 when sorbitan 9-octadecenoate is being prepared.

The esterification temperature should not be above about 240° C. because the amount of color formation is undesirably large when higher temperatures are used. On the other hand, the temperature is ordinarily not below about 180° C. because the reaction becomes too slow and esterification may be incomplete at lower temperatures. Temperatures from about 190° C. to about 210° C. are ordinarily preferable. Even within this range, the rate of reaction is noticeably slower and the color of the product is noticeably better at 190° C. than at 210° C. Reaction times from about 2.5 to about 7.0 hours are ordinarily required. The esterification should be carried out in a substantially anhydrous medium. The reaction is preferably carried out in the presence of activated carbon which serves as a decolorizing agent. The reaction is also preferably carried out in an inert (e.g., nitrogen) atmosphere.

Sodium hydroxide is the preferred alkaline catalyst for esterification, because of its high efficiency and low cost. However, other alkaline materials such as potassium hydroxide, sodium carbonate, sodium acetate, sodium stearate, or trisodium phosphate can be used instead of sodium hydroxide if desired. The amount of alkaline catalyst should be limited so that the final product after neutralization will not contain an undesirably large amount of free fatty acid. The amount of sodium hydroxide used will seldom exceed 1% by weight based on the weight of the product. Even smaller amounts are preferred. Preferably the amount of sodium hydroxide used does not exceed the quantity which is chemically equivalent to the maximum quantity of free acid desired in product. Equivalent quantities of other alkaline materials can be used in place of sodium hydroxide.

When the reaction is completed, reaction may be terminated by cooling the reaction product mixture and adding a small amount of acid, preferably phosphoric acid, sufficient to neutralize the alkali present. Color stability of the product is improved by using at least about one mole of phosphoric acid for every 1.5 moles of sodium hydroxide catalyst used.

An unsaturated glycitan fatty ester obtained according to the present process can be ethoxylated according to procedures known in the art. Ethylene oxide adducts containing an average of about 4 to about 100 or more moles of ethylene oxide per mole of the metathesis-derived unsaturated fatty ester of an intramolecular condensate of a glycitol having four or more carbons can be prepared. The resulting ethylene oxide adducts are known in the art and are useful as hydrophilic surfactants and emulsifiers. Combinations of the unsaturated glycitan fatty ester and the corresponding polyoxyethylene adduct are useful as emulsifying agents, particularly in foods. By appropriate control of the degree of ethoxylation and appropriate choice of the relative amount of the fatty ester and its ethoxylated derivative, a wide range of HLB (hydrophlic/lipophilic balance) values and surfactant effects can be achieved.

EXAMPLES

Example 1 Cross-Metathesis of Soybean Oil with 1-Butene

A clean, dry, stainless steel jacketed 5-gal. Parr reactor vessel equipped with a dip tube, overhead stirrer, internal cooling/heated coils, temperature probe, sampling valve, and headspace gas release valve is purged with argon to 15 psig. Soybean oil (SBO, 2.5 kg, 2.9 mol, Costco, MWn=864.4 g/mol, 85 weight % unsaturation as determined by gas chromatographic analysis ("by gc"), 1 hour argon sparged in 5-gal container) is added into the Parr reactor. The Parr reactor is then sealed and the SBO is purged with argon for 2 hours while cooling to 10° C. After 2 hours, the reactor is vented until the internal pressure reaches 10 psig. The dip tube valve on the reactor is connected to a 1-butene cylinder (Airgas, CP grade, 33 psig headspace pressure, >99 weight %) and re-pressurized to 15 psig of 1-butene. The reactor is vented again to 10 psig to remove residual argon in the headspace. The SBO is stirred at 350 rpm and 9-15° C. under 18-28 psig 1-butene until 3 mol 1-butene per SBO olefin bond is transferred into the reactor (approximately 2.2 kg 1-butene over approximately 4-5 hours). A toluene solution of [1,3-Bis-(2,4,6-trimethylphenyl)-2-imidazolidinylidene] dichlororuthenium(3-methyl-2-butenylidene) (tricyclohexylphosphine) (C827, Material) is prepared in Fischer-Porter pressure vessel by dissolving 130 mg catalyst in 30 grams of toluene as a catalyst carrier (10 mol ppm per olefin bond of SBO) and is added to the reactor via the reactor dip tube by pressurizing the headspace inside the Fischer-Porter vessel to 50-60 psig with argon. The Fischer-Porter vessel and dip tube are rinsed with an additional 30 g toluene. The reaction mixture is stirred for 2.0 hours at 60° C. The reaction mixture is allowed to cool to ambient temperature while the gases in the headspace are vented. After the pressure is released, the reaction mixture is transferred to a 3-neck round bottom flask containing 58 g bleaching clay (2% w/w SBO, Pure Flow B80 CG) and a magnetic stir bar. The reaction mixture is treated by stirring at 85° C. under argon. After 2 hours, during which time any remaining 1-butene is allowed to vent, the reaction mixture is allowed to cool to 40° C. and filtered through a fritted glass filter. An aliquot of the product mixture is found by gas chromatographic analysis (following transesterification with 1% w/w sodium methoxide in methanol at 60° C.) to contain approximately 22 weight % methyl 9-decenoate, approximately 16 weight % methyl 9-dodecenoate, approximately 3 weight % dimethyl 9-octadecenedioate, and approximately 3 weight % methyl 9-octadecenoate (by gc).

Example 2 Production of dimethyl 9-octadecene-1,18-dioate by metathesis

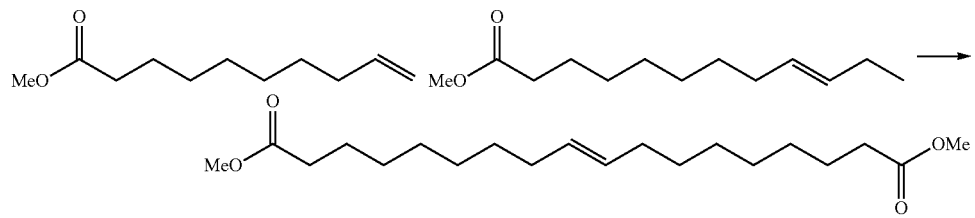

A dibasic ester composition is produced in accordance with the exemplary procedure below, including a cross-metathesis reaction between methyl 9-decenoate (9-decenoic acid methyl ester, 9-DAME) and methyl 9-dodecenoate (9-dodecenoic acid methyl ester, 9-DDAME). A 1.0:1.0 mole ratio mixture of 9-DAME and 9-DDAME (332 g) is charged to a 1 L round bottom flask and heated to 60° C. Pressure is adjusted to 100 mg Hg with ChemGlass diaphragm vacuum pump model CG-4812-30/and J-Kem Scientific Digital Vacuum Regulator Model 200 and stirring is initiated with a magnetic stir bar. After the system stabilizes at desired conditions, 80 ppm of C-827 (as toluene solution) is added (t=0 min). At approximately 15-20 min, the reaction starts bubbling vigorously and the pressure rises to approximately 500 mm Hg. Pressure restabilizes at 100 mm Hg after approximately 5-10 more minutes. At 180 min, an additional 40 ppm of the catalyst C-827 (as toluene solution) is added. Subsequently, the catalyst is deactivated with 25 equivalents tris hydroxymethyl phosphine (THMP) to C-827 at 80° C. for 120 min, THMP. The catalyst is then removed by water extraction (5:1 oil to water). The composition is dried with MgSO4. Then, light FAME stripping is conducted at 1 mm Hg and approximately 100° C. The products from this reaction include a large fraction of 18:1 dibasic ester.

Example 3 Production of 9-decenoic acid from methyl 9-decenoate

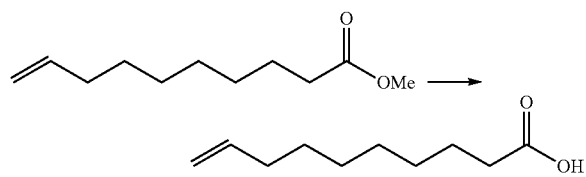

In a 5 L 5-neck round bottom flask, 1108.5 g of methyl 9-decenoate, 540 mL water, and 300 mL isopropanol were combined. The flask was connected to a mechanical stirrer, addition funnel, condenser, thermocouple, and stopper. Nitrogen was passed over the headspace for 20 minutes. An aqueous solution of potassium hydroxide (6.6 moles in 660 mL water) was added over 30 minutes, under an atmosphere of nitrogen, at ambient pressure. The reaction temperature peaked at 54° C. The mixture was stirred for a further 4 hours following the addition of aqueous hydroxide addition. After 4 hours, the temperature of the reaction was 28° C. The flask was placed in a water bath and aqueous hydrochloric acid (HCl, 37% (v/v)) was added in portions over 1 hr until the pH was 1-2. The temperature was kept below 40° C. by adding ice to the water bath during the addition of aqueous HCl. The solution was then transferred to a separatory funnel where the organic layer was washed three times with saturated sodium chloride and dried over magnesium sulfate. The magnesium sulfate was removed via vacuum filtration, and the solution was concentrated on the rotary evaporator. The crude product was distilled under reduced pressure (140° C., 2 torr) to provide 9-decenoic acid (995.2 g, 97% yield) as a colorless liquid.

Example 4 Production of 9-dodecenoic acid from methyl 9-dodecenoate

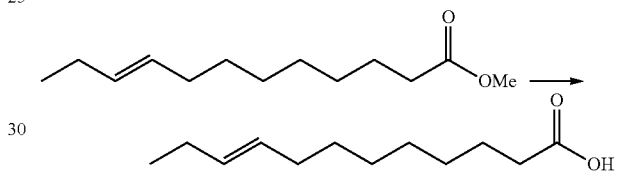

Methyl 9-dodecenoate (1273 g, 6.00 mol), water (540 mL), and isopropanol (300 mL) were added to a 5 L, 4-neck round-bottom flask at room-temperature. The flask was fitted with an over-head stirrer, condenser, a thermocouple, and an addition flask. Nitrogen was passed through the headspace for thirty-minutes while stirring. Potassium hydroxide (10 M, 660 mL, 6.60 mol) was added drop-wise over thirty-minutes. After stirring for about 45 minutes, an exotherm was observed and the mixture became homogenous. Within the next hour, stirring became impeded by formation of a gel. To re-enable stirring, an additional 300 mL of isopropanol was kneaded into the mixture with a metal spatula. The reaction was monitored by thin layer chromatography (10% EtOAc in hexanes eluent, iodine stain); reaction aliquots were quenched with aqueous hydrochloric acid, washed with water, then taken up in iPrOH. When all starting material had been consumed, the reaction was placed in an ice bath and acidified with 37% aqueous HCl (600 mL) while maintaining a temperature below 40° C. The reaction mixture was transferred into a large separatory funnel and washed with brine (3×250 mL), dried with magnesium sulfate, filtered, and dried in vacuo. The reaction was purified by vacuum distillation to give 9-dodecenoic acid (1054 g, 5.3 mol, 89% yield).

Example 5 Preparation of anhydro sorbitol (sorbitan) from sorbitol

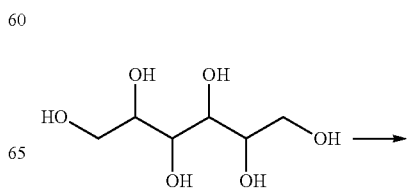

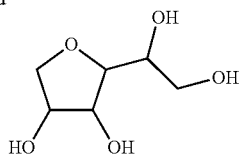

70 wt % aqueous sorbitol (Sorbitol F, 150.0 g, 0.8106 mol) was charged to a dry 500 mL three-neck round bottom flask equipped with a Dean-Stark trap, condenser, thermocouple, heating mantle, nitrogen inlet and outlet. The viscous liquid was warmed under reduced pressure, with magnetic stirring, to remove water. Vacuum was applied at the top of the condenser. A majority of the expected 45.0 g water was removed at an internal temperature of ~40° C. and 40 torr. A final temperature of 90° C. and pressure of 15 torr was observed when the mass at the reactor, and mass of water collected in the Dean-Stark trap, indicated the desired level of dehydration. Ambient pressure was restored with nitrogen then a catalytic amount of p-toluenesulfonic acid monohydrate (1.5270 g, 8.027 mmol) was added to the highly viscous anhydrous sorbitol. The resulting intramolecular etherification mixture was warmed to 120° C. and placed under reduced pressure (35 torr; slight sweep of nitrogen) with continued stirring. After 100 min, the desired mass of water (14.70 g, 0.8157 mol) was collected in the Dean-Stark trap. Ambient pressure was restored to the reactor with nitrogen then potassium hydroxide (0.4516 g, 8.048 mmol, as a 50 wt % aqueous solution) was added to quench the anhydro sorbitol-forming reaction. The mixture was stirred for 15 minutes then tested with a pH indicator strip to confirm neutralization (7.0<pH<8.0). The light amber, molten product was used directly in the subsequent esterification of 9-decenoic acid, as described in Example 6.

Example 6 Production of sorbitan 9-decenoate from 9-decenoic acid

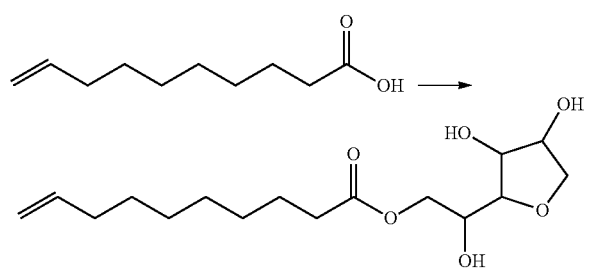

To the reactor containing neutralized anhydro sorbitol (sorbitan, 0.8116 mol) of Example 5 was added 9-decenoic acid (150.1 g, 0.8817 mol) followed by a catalytic amount of potassium hydroxide (0.5049 g, 8.998 mmol, as an approximately 50 wt % aqueous solution), at ca. 90° C. The resulting heterogeneous mixture was warmed to 200° C. over 40 min, at ambient pressure under a nitrogen atmosphere. The contents were digested at this temperature for 6 h, until the acid number of the mixture had been reduced to less than 5 mg KOH/g sample and FTIR analysis of the reaction mixture no longer showed a carboxylic acid C(O) absorption at 1709 cm-1. The clear, straw-colored material was cooled to 120° C. and neutralized by the addition of 85 wt % aqueous phosphoric acid (0.53 mL, 7.7 mmol) via syringe. A turbid mixture was formed on neutralization. The salts from neutralization were removed by vacuum filtration (hot) through a medium porosity glass sintered funnel. Sorbitan 9-decenoate was obtained as a clear, viscous and light orange oil. IR: 3408, 3076, 2927, 2855, 1739, 1640, 1172 cm-1.

Example 7 Production of sorbitan 9-dodecenoate from 9-dodecenoic acid

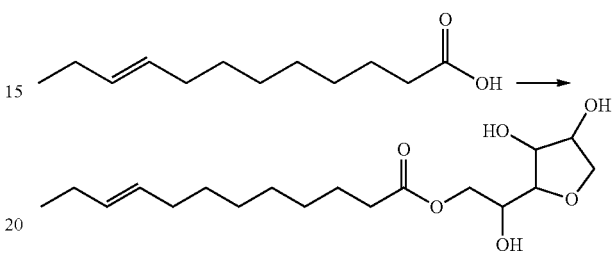

To a 500 mL three-neck round bottom flask equipped with a Dean-Stark trap, condenser, thermocouple, heating mantle, nitrogen inlet and outlet, containing anhydro sorbitol (0.638 mol, prepared as described in Example 6) was added 9-dodecenoic acid (139.3 g, 0.7023 mol). A catalytic amount of potassium hydroxide (0.358 g, 6.38 mmol) was then added at ca. 90° C. The resulting heterogeneous mixture was warmed to 200° C. over 40 min, with magnetic stirring, at ambient pressure under a nitrogen atmosphere. The contents were digested at this temperature for 5 h, until the acid number of the mixture had been reduced to less than 5 mg KOH/g sample and FTIR analysis of the reaction mixture no longer showed a carboxylic acid C(O) absorption at 1709 cm-1. The clear, straw-colored material was cooled to 120° C. and neutralized by the addition of 85 wt % aqueous phosphoric acid (0.51 mL, 7.5 mmol) via syringe. A turbid mixture was formed on neutralization. The salts from neutralization were removed by vacuum filtration (hot) through a medium porosity glass sintered funnel. Sorbitan 9-dodecenoate was obtained as clear, viscous and light orange oil. IR: 3405, 2926, 2854, 1739, 1460, 1079 cm-1.

We claim:
1. A composition comprising the following structure:

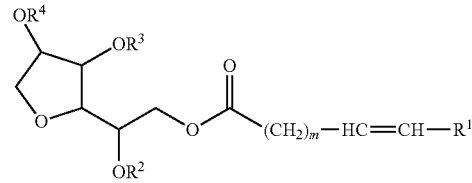

wherein $R^1$ is a hydrogen atom, ethyl, propyl, pentyl, aryl or $(CH_2)_{1-9}$—$COOR^5$; wherein $R^5$ is

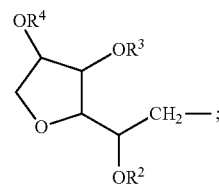

wherein $R^2$, $R^3$ and $R^4$ are independently at each occurrence a hydrogen atom, or —(O)C—$(CH_2)_m$—CH=CH—$R^1$ or —$(CH_2CH_2O)_n$H or mixtures thereof; wherein m is an integer from 1 to 9; and wherein n is an integer from 1 to 100.

2. The composition of claim 1, wherein $R^1$ is a hydrogen atom.

3. The composition of claim 2, wherein the composition comprises sorbitan 9-decenoate.

4. The composition of claim 1, wherein $R^1$ is ethyl.

5. The composition of claim 4, wherein the composition comprises sorbitan 9-dodecenoate.

6. The composition of claim 1, wherein $R^1$ is propyl.

7. The composition of claim 6, wherein the composition comprises sorbitan 9-tridecenoate.

8. The composition of claim 1, wherein $R^1$ is pentyl.

9. The composition of claim 8, wherein the composition comprises sorbitan 9-pentadecenoate.

10. The composition of claim 1, wherein $R^1$ is —$(CH_2)_{1-9}$—$COOR^5$.

11. The composition of claim 10, wherein $R^1$ is —$(CH_2)_7$—$COOR^5$.

12. The composition of claim 11, wherein the composition comprises disorbitan 9-octadecene-1,18-dioate.

* * * * *